US011753623B2

(12) United States Patent
Klassen et al.

(10) Patent No.: US 11,753,623 B2
(45) Date of Patent: Sep. 12, 2023

(54) COMPOSITIONS FOR TREATING RETINAL DISEASES AND METHODS FOR MAKING AND USING THEM

(71) Applicant: The Regents of the University of California, Oakland, CA (US)

(72) Inventors: Henry Klassen, Irvine, CA (US); Jing Yang, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 404 days.

(21) Appl. No.: 16/618,919

(22) PCT Filed: Jun. 5, 2018

(86) PCT No.: PCT/US2018/035981
§ 371 (c)(1),
(2) Date: Dec. 3, 2019

(87) PCT Pub. No.: WO2018/226640
PCT Pub. Date: Dec. 13, 2018

(65) Prior Publication Data
US 2020/0140811 A1 May 7, 2020

Related U.S. Application Data

(60) Provisional application No. 62/515,216, filed on Jun. 5, 2017.

(51) Int. Cl.
*C12N 5/079* (2010.01)
*A61K 9/00* (2006.01)
*A61K 35/30* (2015.01)

(52) U.S. Cl.
CPC .......... *C12N 5/0621* (2013.01); *A61K 9/0019* (2013.01); *A61K 35/30* (2013.01); *C12N 2500/02* (2013.01); *C12N 2500/38* (2013.01); *C12N 2500/90* (2013.01); *C12N 2501/11* (2013.01); *C12N 2501/115* (2013.01); *C12N 2501/602* (2013.01); *C12N 2501/998* (2013.01); *C12N 2509/00* (2013.01); *C12N 2509/10* (2013.01)

(58) Field of Classification Search
None
See application file for complete search history.

(56) References Cited

U.S. PATENT DOCUMENTS

| 9,963,675 B2 | 5/2018 | Klassen et al. |
| 2012/0321593 A1 | 12/2012 | Young et al. |
| 2016/0319243 A1 | 11/2016 | Klassen et al. |

OTHER PUBLICATIONS

Yang et al. "In vitro isolation and expansion of human retinal progenitor cells." Experimental Neurology 177.1 (2002): 326-331. (Year: 2002).*
Extended European Search Report for EP 18814432.3, dated Feb. 16, 2021.

* cited by examiner

*Primary Examiner* — Emily A Cordas
(74) *Attorney, Agent, or Firm* — Greer, Burns & Crain, LTD.; Gregory P. Einhorn

(57) ABSTRACT

Disclosed herein are compositions and methods for treating, ameliorating or preventing a retinal disease or condition; improving a photopic (day light) vision; for improving correcting visual acuity, improving macular function, improving a visual field, or improving scotopic (night) vision by administration of retinal progenitor cells.

14 Claims, No Drawings

COMPOSITIONS FOR TREATING RETINAL DISEASES AND METHODS FOR MAKING AND USING THEM

This application is a national phase application claiming benefit of priority under 35 U.S.C. § 371 to Patent Convention Treaty (PCT) International Application serial number PCT/US2018/035981, filed Jun. 5, 2018, now pending, which claims the benefit of priority to U.S. Provisional Application Ser. No. 62/515,216, filed Jun. 5, 2017. The aforementioned applications are herein expressly incorporated by reference in their entirety and for all purposes.

TECHNICAL FIELD

The subject matter described herein relates generally to the fields of stem cell biology and regenerative medicine.

BACKGROUND

Retinal degeneration refers to the deterioration or degeneration caused by the progressive and irreversible decline and death of photoreceptor cells in the retina. The death of photoreceptor cells can result in blindness.

Thus, a need exists in the art for effective treatments to restore injured and lost photoreceptor cells and restore visual function.

SUMMARY

Provided herein are formulations, products of manufacture and/or compositions for use in a subject (e.g., a human) as a medicament, useful in the treatment of a retinal disease or condition, wherein the formulation, product of manufacture or composition include a cell population containing non-immortal human retinal progenitor cells, wherein the formulation, product of manufacture or composition is made by mechanically and/or enzymatically digesting an obtained sample of human retinal tissue from a human at about 12 weeks to about 28 weeks gestational age to generate a dissociated suspension of cells and cell clusters; culturing the suspension in serum-free media in culture flasks or plates coated with a xeno-free fibronectin, an ornithine, a polylysine, or a laminin at standard oxygen levels for between about 4 and 6 passages, and subsequently culturing the suspension in serum-free media at low oxygen levels for between about an additional 3 and 6 passages, wherein the cells are passaged at between 40% to 90% confluence and treated with an enzyme at each passage to dissociate the cells and adding fresh culture media thereby making non-immortal human retinal progenitor cells, wherein the non-immortal human retinal progenitor cells express one or more markers selected from the group consisting of nestin, Sox2, Ki-67, MHC Class I, MHC Class II, osteopontin (OPN), basic fibroblast growth factor (bFGF), and Fas/CD95, wherein nestin is expressed by greater than 90% of the cells in the population, wherein Sox2 is expressed by greater than 80% of the cells in the population, wherein Ki-67 is expressed by greater than 30% of the cells in the population, wherein MHC Class I is expressed by greater than 70% of the cells in the population, wherein Fas/CD95 is expressed by greater than 30% of the cells in the population, wherein MHC Class II is expressed by less than 2% of the cells in the population, wherein osteopontin (OPN) is expressed in an amount greater than about 20 ng/$10^6$ cells/24 hours by the cells in the population, and wherein basic fibroblast growth factor (bFGF) is expressed in an amount between about 50 and about 300 pg/$10^6$ cells/hour by the cells in the population, when the cells are present in a carrier that did not include bFGF at baseline. The cells in the population may additionally express mesencephalic astrocyte-derived neurotrophic factor (MANF) (e.g., in an amount between about 0.5 and about 2.5 ng/$10^6$ cells/24 hours)), pigment epithelium-derived growth factor (PEDF) (e.g., in an amount up to about 30 ng/$10^6$ cells/24 hours), pleiotrophin (PTN) (e.g., in an amount between about 50 and about 600 pg/$10^6$ cells/24 hours); and/or midkine (MDK) (e.g., in an amount up to about 12 ng/$10^6$ cells/24 hours).

In any of the formulations, products of manufacture or compositions disclosed herein, following the subsequent culture culturing of the suspension at low oxygen levels, the cells are allowed to grow without passaging for a period of time (e.g., between about 1 hour and 5 days) at standard oxygen levels.

Suitable low oxygen levels may include, for example, 0.5%, 1%, 1.5%, 2%, 2.5%, 3%, 3.5%, 4%, 4.5%, 5%, 5.5%, 6%, 6.5%, 7%, 7.5%, 8.0%, 8.5%, 9.0%, 9.5%, or 10% oxygen.

In some embodiments, between 0.01 mg/ml and 0.5 mg/ml vitamin C is included in the culture media changed every 1 to 2 days.

These formulations, products of manufacture or compositions for use can be formulated for injection into a vitreous cavity or a subretinal space of the subject.

The retinal disease or condition may be, for example, retinitis pigmentosa (RP), Leber's congenital amaurosis (LCA), Stargardt disease, Usher's syndrome, choroideremia, a rod-cone or cone-rod dystrophy, a ciliopathy, a mitochondrial disorder, progressive retinal atrophy, a degenerative retinal disease, age related macular degeneration (AMD), wet AMD, dry AMD, geographic atrophy, a familial or acquired maculopathy, a retinal photoreceptor disease, a retinal pigment epithelial-based disease, diabetic retinopathy, cystoid macular edema, uveitis, retinal detachment, traumatic retinal injury, iatrogenic retinal injury, macular holes, macular telangiectasia, a ganglion cell disease, an optic nerve cell disease, glaucoma, optic neuropathy, ischemic retinal disease, retinopathy of prematurity, retinal vascular occlusion, familial macroaneurysm, a retinal vascular disease, an ocular vascular diseases, a vascular disease, or ischemic optic neuropathy.

In some embodiments, the cells in the formulations, products of manufacture or compositions further express one or more markers selected from the group consisting of vimentin, CD9, CD81, AQP4, CXCR4, CD15/LeX/SSEA1, GD2 ganglioside, CD133, 03-tubulin, MAP2, GFAP, OPN/SPP1, PTN, KDR, and TEK.

Also provided are methods of making a formulation, product of manufacture or composition containing a heterogeneous mixture of non-immortal human fetal neural retinal cells, by (a) mechanically and/or enzymatically dissociating an obtained sample of human retinal tissue cells from a human about 12 weeks to about 28 weeks gestational age to generate a dissociated suspension of cells and/or cell clusters, wherein the harvested sample of cells and/or small cellular clusters are enzymatically dissociated using trypsin or equivalent; (b) culturing the suspension in serum-free media in culture flasks or plates coated with a xeno-free fibronectin, an ornithine, a polylysine, or a laminin at standard oxygen levels for between about 4 and 6 passages; and (c) subsequently culturing the suspension in serum-free media at low oxygen levels for between about an additional 3 and 6 passages, wherein the cells are passaged at between 40% to 90% confluence and treated with an enzyme at each passage to dissociate the cells and the culture media is changed about every 1 to 2 days.

In some embodiments, following the subsequent culture culturing of the suspension at low oxygen levels, the cells are allowed to grow without passaging for a period of time (e.g., between 1 hour and 5 days) at standard oxygen levels.

Suitable low oxygen levels may include, for example, 0.5%, 1%, 1.5%, 2%, 2.5%, 3%, 3.5%, 4%, 4.5%, 5%, 5.5%, 6%, 6.5%, 7%, 7.5%, 8.0%, 8.5%, 9.0%, 9.5%, or 10% oxygen.

In any of these methods, between 0.01 mg/ml and 0.5 mg/ml vitamin C is included in the culture media changed every 1 to 2 days.

The cells and/or cell clusters are cultured in a basal culture medium, optionally together with supplements or additives that support cell survival or growth. By way of non-limiting example, the supplements or additives that support cell survival or growth are selected from the group consisting of L-glutamine, human recombinant growth factors consisting of EGF and bFGF (Invitrogen), and other growth factors. In some embodiments, the media is supplemented with albumin, or recombinant albumin in an amount to have an initial concentration of about 1.0 mg/ml).

The sample of cells is screened for the presence of a pathogen, a bacteria, an endotoxin, a fungus, a mycoplasma, a virus, a hepatitis virus or an HIV virus; for the presence of a normal karyotype; for viability; and/or for tumorigenicity. In some embodiments, the sample of cells additionally or alternatively does not exhibit elevated telomerase activity.

These methods may also involve the steps of (a) selecting human fetal neural retinal cells on the basis of cell surface or genetic markers, and/or (b) selecting human fetal neural retinal cells on the basis of a human fetal neural retinal cell transcriptome profile, proteome profile or a genomic profile. For example, step (a) may additionally involve selecting the cells either before culturing (prospectively) or after culturing or both; the cell surface or genetic markers include CD15/LeX/SSEA1 and/or GD2 ganglioside; and/or the cell surface or genetic markers include CD9, CD81, CD133 or AQP4 and/or CXCR4.

Additionally provided are methods for isolating a population of non-immortal human retinal progenitor cells involving mechanically and/or enzymatically dissociating a sample of human retinal tissue that is from a stage after the retina is formed but before photoreceptor outer segments are fully formed throughout the retina and before retinal vascularization is substantially completed or completed to generate a dissociated suspension of cells and cell clusters; culturing the suspension in serum-free media in culture flasks or plates coated with a xeno-free fibronectin, an omithine, a polylysine, or a laminin at standard oxygen levels for between about 4 and 6 passages; and subsequently culturing the suspension in serum-free media at low oxygen levels for between about an additional 3 and 6 passages, wherein the cells are passaged at between 40% to 90% confluence and treated with an enzyme at each passage to dissociate the cells, wherein the human retinal progenitor cells express one or more markers selected from the group consisting of nestin, Sox2, Ki-67, MHC Class I, MHC Class II, osteopontin (OPN), and Fas/CD95, wherein nestin is expressed by greater than 90% of the cells in the population, wherein Sox2 is expressed by greater than 80% of the cells in the population, wherein Ki-67 is expressed by greater than 30% of the cells in the population, wherein MHC Class I is expressed by greater than 70% of the cells in the population, wherein Fas/CD95 is expressed by greater than 30% of the cells in the population, wherein MHC Class II is expressed by less than 2% of the cells in the population, wherein osteopontin (OPN) is expressed in an amount greater than about 20 ng/$10^6$ cells/24 hours by the cells in the population, and wherein basic fibroblast growth factor (bFGF) is expressed in an amount between about 50 and about 300 pg/$10^6$ cells/hour by the cells in the population, when the cells are present in a carrier that did not include bFGF at baseline. The cells in the population may additionally express mesencephalic astrocyte-derived neurotrophic factor (MANF) (e.g., in an amount between about 0.5 and about 2.5 ng/$10^6$ cells/24 hours), pigment epithelium-derived growth factor (PEDF) (e.g., in an amount up to about 30 ng/$10^6$ cells/24 hours), pleiotrophin (PTN) (e.g., in an amount between about 50 and about 600 pg/$10^6$ cells/24 hours); and/or midkine (MDK) (e.g., in an amount up to about 12 ng/$10^6$ cells/24 hours).

In some embodiments, following the subsequent culture culturing of the suspension at low oxygen levels, the cells are allowed to grow without passaging for a period of time (e.g., between about 1 hour and 5 days) at standard oxygen levels.

Suitable low oxygen levels may include, for example, 0.5%, 1%, 1.5%, 2%, 2.5%, 3%, 3.5%, 4%, 4.5%, 5%, 5.5%, 6%, 6.5%, 7%, 7.5%, 8.0%, 8.5%, 9.0%, 9.5%, or 10% oxygen.

In any of these methods, the culture media is changed every 1 to 2 days.

In any of these methods, between 0.01 mg/ml and 0.5 mg/ml of vitamin C is included in the culture media changed every 1 to 2 days.

The human retinal tissue can be obtained from a human fetal retina at a gestational age between about 12 weeks to about 28 weeks.

In some embodiments of these methods, the cells are cultured in serum-free or reduced serum cell culture media. This media may additionally contain albumin.

The cells in the population further express one or more markers selected from the group consisting of vimentin, CD9, CD81, AQP4, CXCR4, CD15/LeX/SSEA1, GD2 ganglioside, CD133, 03-tubulin, MAP2, GFAP, OPN/SPP1, PTN, KDR, and TEK.

Also provided are methods for treating, ameliorating, preventing or slowing the progress of a retinal disease or condition in a patient (e.g., a human) by administering an effective amount of a formulation, product of manufacture or composition for use, wherein the formulation, product of manufacture or composition that includes a cell population containing non-immortal human retinal progenitor cells, wherein the formulation, product of manufacture or composition is made by mechanically and/or enzymatically digesting an obtained sample of human retinal tissue from a human at about 12 weeks to about 28 weeks gestational age to generate a dissociated suspension of cells and cell clusters; and culturing the suspension in serum-free media in culture flasks or plates coated with a xeno-free fibronectin, an omithine, a polylysine, or a laminin at standard oxygen levels for between about 4 and 6 passages, and subsequently culturing the suspension in serum-free media at low oxygen levels for between about an additional 3 and 6 passages, wherein the cells are passaged at between 40% to 90% confluence and treated with an enzyme at each passage to dissociate the cells and adding fresh culture media thereby making non-immortal human retinal progenitor cells, wherein the non-immortal human retinal progenitor cells express one or more markers selected from the group consisting of nestin, Sox2, Ki-67, MHC Class I, MHC Class II, osteopontin (OPN), and Fas/CD95, wherein nestin is expressed by greater than 90% of the cells in the population, wherein Sox2 is expressed by greater than 80% of the cells in the population, wherein Ki-67 is expressed by greater than 30% of the cells in the population, wherein MHC Class I is expressed by greater than 70% of the cells in the population, wherein Fas/CD95 is expressed by greater than 30% of the cells in the population, wherein MHC Class II is expressed by less than 2% of the cells in the population, wherein osteopontin (OPN) is expressed in an amount greater than about 20 ng/$10^6$ cells/24 hours by the cells in the population, and wherein basic fibroblast growth factor (bFGF) is expressed in an amount between about 50 and about 300 pg/$10^6$ cells/hour by the cells in the population, when the cells are present in a carrier that did not include bFGF at baseline. The cells in the population may additionally express mesencephalic astrocyte-derived neurotrophic factor (MANF) (e.g., in an amount between about 0.5 and about 2.5 ng/$10^6$ cells/24 hours), pigment epithelium-derived growth factor (PEDF) (e.g., in an amount up to about 30 ng/$10^6$ cells/24 hours), pleiotrophin (PTN) (e.g., in an amount between about 50 and about 600 pg/$10^6$ cells/24 hours); and/or midkine (MDK) (e.g., in an amount up to about 12 ng/$10^6$ cells/24 hours).

In some embodiments, following the subsequent culture culturing of the suspension at low oxygen levels, the cells are allowed to grow without passaging for a period of time (e.g., between about 1 hour and 5 days) at standard oxygen levels.

Suitable low oxygen levels may include, for example, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% oxygen.

In any of these methods, between 0.01 mg/ml and 0.5 mg/ml vitamin C is included in the culture media changed every 1 to 2 days.

The formulation, product of manufacture or composition is injected into a vitreous cavity or a subretinal space of the patient. In some embodiments, the formulation, product of manufacture or composition is injected into the anterior region of the vitreous cavity and/or into the posterior region of the vitreous cavity.

The retinal disease or condition may include retinitis pigmentosa (RP), Leber's congenital amaurosis (LCA), Stargardt disease, Usher's syndrome, choroideremia, a rod-cone or cone-rod dystrophy, a ciliopathy, a mitochondrial disorder, progressive retinal atrophy, a degenerative retinal disease, age related macular degeneration (AMD), wet AMD, dry AMD, geographic atrophy, a familial or acquired maculopathy, a retinal photoreceptor disease, a retinal pigment epithelial-based disease, diabetic retinopathy, cystoid macular edema, uveitis, retinal detachment, traumatic retinal injury, iatrogenic retinal injury, macular holes, macular telangiectasia, a ganglion cell disease, an optic nerve cell disease, glaucoma, optic neuropathy, ischemic retinal disease, retinopathy of prematurity, retinal vascular occlusion, familial macroaneurysm, a retinal vascular disease, an ocular vascular diseases, a vascular disease, or ischemic optic neuropathy.

By way of non-limiting example, the effective amount is between 0.3-0.5×$10^6$ cells or between 0.5-3×$10^6$ cells.

These methods may also involve use of surgical vitrectomy, core vitrectomy, a vitreolytic agent, or a combination thereof in conjunction with the administration of the effective amount of a formulation, product of manufacture or composition for use.

In any of these methods, the patient can receive at least one subsequent dose of the formulation, product of manufacture or composition for use into either the same eye or the fellow eye of the patient.

With any of the methods described herein, photopic (day light) vision, visual acuity, macular function, visual field, scotopic (night) vision, or any combination thereof is improved in the patient following administration of the formulation, product of manufacture or composition for use.

The administration of the formulation, product of manufacture or composition for use may also result in one or more of the following: (i) enhanced activation of Mueller cells; (ii) increased local expression of glutamine synthetase; (iii) reduced vascular permeability; (iv) reduced occurrence of ischemia; (v) enhanced recruitment of macrophages in retinal degeneration; (vi) increased local expression of bFGF in retinal degeneration; and/or (vii) decreased expression of caspase 3.

Any of the aspects and embodiments described herein can be combined with any other aspect or embodiment as disclosed here in the Summary of the Invention, in the Drawings, and/or in the Detailed Description of the Invention, including the below specific, non-limiting, examples/embodiments of the present invention.

Unless otherwise defined, all technical and scientific terms used herein have the same meaning as commonly understood by one of ordinary skill in the art to which this application belongs. In the specification, the singular forms also include the plural unless the context clearly dictates otherwise.

Although methods and materials similar to or equivalent to those described herein can be used in the practice and testing of the application, suitable methods and materials are described below. All publications, patent applications, patents, and other references mentioned herein are hereby expressly incorporated by reference for all purposes.

The references cited herein are not admitted to be prior art to the claimed application. In the case of conflict, the present specification, including definitions, will control. In addition, the materials, methods, and examples are illustrative only and not intended to be limiting.

The features, structures, or characteristics described throughout this specification may be combined in any suitable manner in one or more embodiments. For example, the usage of the phrases "exemplary embodiments," "example embodiments," "some embodiments," or other similar language, throughout this specification refers to the fact that a particular feature, structure, or characteristic described in connection with an embodiment may be included in at least one embodiment described herein. Thus, appearances of the phrases "exemplary embodiments," "example embodiments," "in some embodiments," "in other embodiments," or other similar language, throughout this specification do not necessarily all refer to the same group of embodiments, and the described features, structures, or characteristics can be combined in any suitable manner in one or more embodiments.

Other features and advantages of the application will become apparent from the following detailed description in conjunction with the examples.

DETAILED DESCRIPTION

Definitions

To facilitate the understanding of this disclosure, a number of terms are defined below. The terminology herein is used to describe specific embodiments of the subject matter described herein, but their usage does not delimit the subject matter, except as outlined in the claims.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

Unless specifically stated or obvious from context, as used herein, the terms "a," "an," and "the" are understood to be singular or plural.

Unless specifically stated or obvious from context, as used herein, the term "or" is understood to be inclusive.

As used herein in other contexts, the term "about," unless indicated otherwise, refers to the recited value, e.g., amount, dose, temperature, time, percentage, etc., +/−10%, +/−9%, +/−8%, +/−7%, +/−6%, +/−5%, +/−4%, +/−3%, +/−2%, or +/−1%.

In alternative embodiments, as used herein, the terms "patient" or "subject" and the like are used interchangeably herein to refer to any mammal, including humans, domestic and farm animals, and zoo, sports, and pet animals, such as dogs, horses, cats, and agricultural use animals including cattle, sheep, pigs, and goats. One preferred mammal is a human, including adults, children, and the elderly. A subject may also be a pet animal, including dogs, cats and horses. Preferred agricultural animals would be cattle and goats.

In alternative embodiments, the terms "treat", "treating", "treatment" and the like, as used herein, unless otherwise indicated, refers to curing, reversing, attenuating, alleviating, minimizing, inhibiting the process of, suppressing, halting, and/or preventing the disease, disorder or condition to which such term applies, or one or more (i.e., not necessarily all) symptoms of such disease, disorder or condition and includes the administration of any of the compositions, pharmaceutical compositions, or dosage forms described herein, to prevent the onset of the symptoms or the complications, alleviating the symptoms or the complications, attenuating the progression of, and/or eliminating the disease, condition, or disorder. Preferably, treatment is curative or ameliorating.

In alternative embodiments, as used herein, "preventing" or "prophylaxis" means preventing in whole or in part, or ameliorating or controlling, or reducing or halting the production or occurrence of the thing or event, for example, the disease, disorder or condition, to be prevented.

In alternative embodiments, the phrases "therapeutically effective amount" and "effective amount" and the like, as used herein, indicate an amount necessary to administer to a patient, or to a cell, tissue, or organ of a patient, to achieve a therapeutic effect, such as an ameliorating or alternatively a curative effect. The effective amount is sufficient to elicit the biological or medical response of a cell, tissue, system, animal, or human that is being sought by a researcher, veterinarian, medical doctor, or clinician. Determination of the appropriate effective amount or therapeutically effective amount is within the routine level of skill in the art.

In alternative embodiments, the terms "administering", "administer", "administration" and the like, as used herein, refer to any mode of transferring, delivering, introducing, or transporting a therapeutic agent to a subject in need of treatment with such an agent. Such modes include, but are not limited to, intraocular, oral, topical, intravenous, intraarterial, intraperitoneal, intramuscular, intradermal, intranasal, and subcutaneous administration.

In alternative embodiments, as used herein, the terms "purified" or "enriched" or the like indicates that the cells or cell populations are removed from their normal tissue environment and are present at a higher concentration as compared to the normal tissue environment. Accordingly, a "purified" or "enriched" cell population may further include cell types in addition to retinal progenitor cells and may include additional tissue components, and the term "purified" or "enriched" does not necessarily indicate the presence of only progenitor cells or exclude the presence of other cell types.

In alternative embodiments, the retinal progenitor cell populations as disclosed herein may be at least 5% pure, at least 10% pure, at least 15% pure, at least 20% pure, least 25% pure, at least 30% pure, at least 35% pure, at least 40% pure, at least 45% pure, at least 50% pure, at least 55% pure, at least 60% pure, at least 65% pure, at least 70% pure, at least 75% pure, at least 80% pure, at least 85% pure, at least 90% pure, at least 95% pure, at least 96% pure, at least 97% pure, at least 98% pure, at least 99% pure or at any increment between 5% and 99% pure (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%).

In alternative embodiments, a "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 Daltons). In alternative embodiments, retinal progenitor cells may be characterized by the presence of one or more markers that can be expressed on the surface of the cells within the cell population (a "cell surface marker"), inside cells within the cell population (i.e., in the nucleus or cytoplasm of a cell), and/or expressed at the RNA or protein level as a "genetic" marker.

In alternative embodiments, the terms "express" and "expression" as used herein refers to transcription and/or translation of a nucleic acid sequence within a host cell. The level of expression of a desired product/protein of interest in a host cell may be determined or "screened" on the basis of either the amount of corresponding mRNA that is present in the cell, or the amount of the desired polypeptide/protein of interest encoded by the selected sequence as in the present examples. For example, mRNA transcribed from a selected sequence can be quantified or detected by Northern blot hybridization, ribonuclease RNA protection, in situ hybridization to cellular RNA, microarray analysis, or by reverse-transcription polymerase chain reaction (RT-PCR). Proteins encoded by a selected sequence can be detected or quantified by various antibody-based methods, e.g. by ELISA, by Western blotting, by radioimmunoassays, by immunoprecipitation, by assaying for the biological activity of the protein, by immunostaining of the protein (including, e.g., immunohistochemistry and immunocytochemistry), by flow cytometry or fluorescence activated cell sorting ("FACS") analysis, or by homogeneous time-resolved fluorescence (HTRF) assays.

Retinal Progenitor Cells (RPCs)

In alternative embodiments, the isolation, characterization, and use of mammalian retinal progenitor cells is as described in detail in WO 2012/158910, which is herein incorporated by reference in its entirety.

In vertebrate embryonic development, the retina and the optic nerve originate as outgrowths of the developing brain, so the retina is considered part of the central nervous system (CNS) and is actually brain tissue. The retina is a layered structure with several layers of neurons interconnected by synapses. From closest to farthest from the vitreous body, that is, from closest to the front exterior of the head towards the interior and back of the head, the retinal layers include the inner limiting membrane including Muller cell footplates, the nerve fiber layer containing axons of the ganglion cell nuclei, the ganglion cell layer, which contains nuclei of ganglion cells, the axons of which become the optic nerve fiber, the inner plexiform layer that contains the synapse between the bipolar cell axons and the dendrites of the ganglion and amacrine cells, the inner nuclear layer, which contains the nuclei and surrounding cell bodies (perikarya) of the bipolar cells, the outer plexiform layer, containing projections of rods and cones ending in the rod spherule and cone pedicle, respectively, the outer nuclear layer, which contain cell bodies of rods and cones, the external limiting membrane, which separates the inner segment portions of the photoreceptors from their cell nucleus, the photoreceptor layer, and the retinal pigment epithelium (RPE), which is a single layer of cuboidal cells. The neurons that are directly sensitive to light are the photoreceptor cells, comprised mainly of two types: the rods and cones. Rods function mainly in dim light and provide black-and-white vision, while cones support daytime vision and the perception of color. A third type of photoreceptor is the photosensitive ganglion cell, is important for reflexive responses to bright daylight.

Donor fetal retinal cells (e.g., the retinal progenitor cells described herein) can provide atrophic influence for the host retina, notably including host cones. This trophic effect is not only neuroprotective but also has a rapid revitalizing effect on residual host retinal cells as determined by improved visual function. Donor cells are capable of integrating into the retina and, via cellular differentiation, replace photoreceptors (which can be in limited numbers). The overall effect is to both rapidly and sustainably restore and preserve clinically significant degrees of visual function in a retina otherwise destined to fail completely, leaving the patient completely blind. Accordingly, any of the compositions and methods described herein can be used to rapidly and sustainably restore and preserve clinically significant degrees of visual function in a retina in a mammal, e.g., a human. For example, any of the compositions and methods described herein can provide clinically significant trophic influences to a diseased retina, or provide regenerative influences to a macular and/or a scotopic visual function.

The cells in the compositions and populations described herein are a population of closely related cells, rather than an isolated single cell type.

While these cells are not stem cells per se (because they do not meet the definition for true stem cells), they are immature and/or plastic. However, these cells cannot (in the absence of additional manipulation) give rise to a germ layer and/or cannot (in the absence of additional manipulation) give rise to all three (3) germ layers.

Additionally, these cells are pre-specified to make retinal tissue or cells. Thus, these cells may express progenitor markers and retinal markers.

Retinal progenitor cells are not pluripotent and can appear to be multipotent. However, because the cells have never been cultured in a pluripotent state, they are, therefore, safer. While, in some embodiments, mammalian fetal retinal cells or RPC cells can be derived artificially from pluripotent cell lines, they optionally contain no population of residual pluripotent cell types.

The cells described herein are retinal progenitor cells (RPCs), which can be distinguished from a neural progenitor and/or a neural stem cells (NSCs). Specifically, such mammalian fetal retinal or RPC cells are multipotent but are not equivalent to NSCs. For example, mammalian fetal retinal or RPC cells are not from the brain, but are from the retina. Additionally, mammalian fetal retinal or RPC cells give rise to photoreceptors, whereas brain-derived progenitors are poor at giving rise to photoreceptors. Likewise, unlike NSCs, mammalian fetal retinal or RPC cells are multipotent but do not (in the absence of additional manipulation) give rise to oligodendrocytes. For example, the mammalian fetal retinal cells or RPC cells give rise to (differentiate into) retinal cells including photoreceptors but not to oligodendrocytes.

Mammalian fetal retinal or RPC cells are obtained (or are obtainable) from a mammalian fetal neural retina, not from a ciliary margin, ciliary epithelium, or RPE. Additionally, mammalian fetal retinal or RPC cells are not descended from differentiated Mueller glia, are not post-mitotic precursors per se, are not stem cells per se, and/or are not a single isolated cell type per se.

Mammalian fetal retinal cells or RPC cells are not found in the early embryo (e.g., the blastocyst). Additionally, mammalian fetal retinal cells or RPC cells are not found in any useful abundance in the normal mature mammal (e.g., human).

In addition, retinal progenitor cells do not persist for the life of the organism. However, these mammalian fetal retinal cells or RPC cells are found in their native abundance in the developing (fetal) mammalian (e.g., human) retina.

While mammalian fetal retinal cells or RPC are mostly mitotic when grown under proliferation conditions, a minority admixture of post-mitotic cells may also be included in any of the compositions and populations described herein.

The mammalian fetal retinal cells or RPC cells are immunologically tolerated as ocular allografts in unrelated mammals, e.g., humans. Thus, the RPCs have low immunogenicity when placed in the eye. By way of non-limiting example, these mammalian fetal retinal cells or RPC cells can be grafted to a vitreous cavity or in a subretinal space for mammalian, or human, vision or retinal disease therapeutic and/or prophylactic therapy.

Preferably, the mammalian fetal retinal cells or RPC cells do not come with any risk (or without a substantial risk) of tumor formation or other unwanted cell growth.

In alternative embodiments, the mammalian fetal retinal cells or RPC cells are cultured as spheres or adherent monolayers, or as spheres and then monolayers, and/or as a combination of spheres and monolayers. However, spheres are not required, and, in some embodiments, the cells are grafted as dissociated cells, not as spheres, or as a mixture of both dissociated cells and spheres. The mammalian fetal retinal cells or RPC cells contain grafted cells that coalesce in the vitreous and, optionally, can become spheres.

In alternative embodiments, retinal progenitor cells and cell populations containing them are not immortal, nor are they allowed to immortalize, or forced to immortalize. While the cells do not proliferate indefinitely, the exemplary cell culture methods described herein can improve the proliferation rate and duration and/or can improve donor cell yield significantly for a given tissue donation.

RPCs can either be non-genetically modified cells, or they can be genetically modified (e.g., transformed stably or transiently, or inducibly) using any method(s) known in the art. For example, retinal progenitor cells can be genetically modified to express one or more heterologous or exogenous nucleic acid sequences of interest. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. In alternative embodiments, nucleic acid sequences include plasmids, amplicons, cDNA, mRNA, antisense RNA, siRNA, but are not limited to these examples. The term "gene" refers to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants.

Any methodology known in the art can be used for genetically altering the cells. One exemplary method is to insert a gene into the cells of the tissue with a recombinant viral vector. Any one of a number of different vectors can be used, such as viral vectors, plasmid vectors, linear DNA, etc., as known in the art, to introduce an exogenous nucleic acid fragment encoding for a therapeutic agent into target cells and/or tissue. These vectors can be inserted, for example, using any of infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound and others as known in the art.

In alternative embodiments, as used herein, a "vector" refers to a carrier nucleic acid molecule into which a nucleic acid sequence can be inserted for introduction into a cell where it can be replicated. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences. In addition to encoding a modified polypeptide, a vector may encode non-modified polypeptide sequences such as a tag or targeting molecule. Useful vectors encoding such fusion proteins include pIN vectors, vectors encoding a stretch of histidines, and pGEX vectors, for use in generating glutathione S-transferase (GST) soluble fusion proteins for later purification and separation or cleavage.

Vectors may be designed primarily to introduce into cells a heterologous nucleic acid molecule, such as a gene that is "operably linked" or under the control of one or more control sequences. In alternative embodiments a "promoter" refers to one or more transcriptional control modules that are clustered around the initiation site for RNA polymerase II and other transcriptional activator proteins. Any promoter/enhancer combination (as per the Eukaryotic Promoter Data Base EPDB) could also be used to drive expression of a nucleic acid molecule of interest (i.e., constitutive, inducible, repressible, tissue specific). Also, the vectors may contain a selectable marker to facilitate their manipulation in vitro or ex vivo. Vectors may also contain a polyadenylation signal, which may be obtained from the human growth hormone (hGH) gene, the bovine growth hormone (BGH) gene, or SV40. In addition, vectors may also contain internal ribosome binding sites (IRES) elements are used to create multigene, or polycistronic, messages. IRES elements are able to bypass the ribosome scanning model of 5-methylated cap-dependent translation and begin translation at internal sites (Pelletier, J. and Sonenberg, N. (1988) Nature 334 (6180): 320-325). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In some embodiments, the vector is a viral vector. Viral vectors known in the art include, without limitation, adenoviral vectors, retroviral vectors, vaccinia viral vectors, adeno-associated viral vectors, polyoma viral vectors, alphaviral vectors, rhabdoviral vectors, lentiviral vectors, Epstein-Barr viral vectors, picornaviral vectors, or herpesviral vectors.

In other embodiments, a nucleic acid sequence may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh, P. C. and Bachhawat, B. K. (1991) Targeted Diagn. Ther. 4: 87-103). One example of a commercially available liposomes or lipid formulations is LIPOFECTAMINE™ (Invitrogen). Others include FUGENE™ (Promega), PROMOFECTIN™ (PromoKine), EFFECTENE™ (Qiagen), POLYFECT™ (Qiagen), SUPERFECT™ (Qiagen), and TRANSMESSENGER™ (Qiagen).

Isolation and Culture of RPCs

Also provided are methods for making, isolating, and/or using dissociated suspensions of fetal retinal cells, e.g., human retinal progenitor cells (hRPCs). In various embodiments, the suspensions of fetal retinal cells do not include tissue or scaffolds.

Cell populations may be harvested from healthy subjects (i.e., individuals not harboring a retinal disease), from diseased subjects, and may include not only fresh retinal cell populations, but also frozen retinal cell populations. Sources include, without limitation, whole eyes, or retinal tissues, or other sources, obtained from embryonic, fetal, pediatric or adult tissue. The methods described herein can include further enrichment or purification procedures or steps for cell isolation by positive selection for other retinal progenitor cell specific markers. The retinal progenitor cells and cell populations may be obtained or harvested from any mammalian species or subjects, e.g. human, primate, equine, bovine, porcine, canine, feline, ferret, rabbit, rodent, e.g. mice, rats, hamster, etc.

In some embodiments, cells are harvested from a mammalian fetal retina at a stage after which the retina is formed, but before photoreceptor outer segments are fully formed throughout the retina and before retinal vascularization has been completed or substantially completed. The stages are typically between fetal gestational ages of about 12 weeks to about 28 weeks (e.g., about 12, 13, 14, 15, 16, 17, 18, 19, 20, 21, 22, 23, 24, 25, 26, 27, or 28 weeks) in a human fetus. For non-human cells from larger mammals, such as feline or porcine retinal progenitor cells, the stages are typically between fetal gestational ages of about 3 weeks to about 11 weeks (e.g., about 3, 4, 5, 6, 7, 8, 9, 10, or 11 weeks). See, for example, Anand-Apte, B. and Hollyfield, J. G. "Developmental Anatomy of the Retinal and Choroidal Vasculature." In The Retina and Its Disorders, Besharse, J. and Bok, D., Academic Press, (2001). However, cells can also be harvested from postnatal or neonatal mammalian tissue.

Retinal progenitor cells can be purified from other tissue components after or concurrent with the processing of a tissue sample. For example, progenitor cells can be purified from other cells and tissue components after the tissue sample has been cultured under conditions suitable for cell growth and for a time sufficient to allow cells to adhere to the culture dish. In certain embodiments, purification of cells involves obtaining cells that migrate from the tissue sample during culture and are present in the culture media or loosely adhered to a fibronectin or other substrate, or a feeder cell layer. These cells may be obtained by routine methods, such as removing and centrifuging the media to pellet cells therein, and washing the cells remaining in the culture dish with a solution such as phosphate-buffered saline (PBS) or Hanks Balanced Salt Solution to remove those cells loosely attached as an adherent cell layer. This wash solution may then also be centrifuged to obtain cells. Purification of retinal progenitor cells and cell populations may further involve separating cells from certain insoluble tissue components, including residual tissue material, such as lipids. Cells may be separated from other tissue components by any means known and available in the art, including, e.g., the use of density gradients, centrifugation, sorting by flow cytometry or magnetic cell separation (MACS), and filtration or combinations thereof. Examples of specific methods of purifying cells are known and described in the art, e.g., in U.S. Pat. No. 6,777,231. Negative separation methods can also be employed to remove one or more particular types of cells.

Tissue may also be processed or "dissociated". Dissociation may be carried out by physical dissociation and/or by exposure to an enzyme preparation that facilitates the release of cells from other tissue components to create a "dissociated suspension" of cells and/or cell clusters. Examples of such enzymes include, but are not limited to, matrix metalloproteinases, clostripain, papain, trypsin, trypsin-like, pepsin, pepsin-like, neutral protease-type and collagenases. Suitable proteolytic enzymes are described in U.S. Pat. Nos. 5,079,160; 6,589,728; 5,422,261; 5,424,208; and 5,322,790. For example, the enzyme preparation may include trypsin alone or in combination with one or more additional enzymes. Enzymatic dissociation may be carried out in conjunction with physical dissociation by, for example, mincing, pipetting, chopping, homogenizing, grinding, freeze-thawing, osmotically shocking, to remove unwanted cells or connective tissue and ultimately resulting in single cell cultures or may include cell clusters that can be defined by size, i.e., "small", "medium" and "large". Cell cluster size is subjective and may vary in the practice of the subject matter disclosed herein.

Also provided are methods for the isolation and characterization of mammalian retinal progenitor cells and compositions containing such cells that are harvested from donor tissue, grown in culture, and formulated for administration to a subject or patient.

Mammalian fetal retinal or RPC cells express quantitatively different gene profiles, e.g., as described herein; or they express quantitatively different soluble factor profiles; or they express quantitatively different surface marker profiles. Moreover, mammalian fetal retinal cells or RPC cells have a gene profile that is not fixed, constant or immutable. Rather, they have a gene profile that dynamically changes quantitatively with time in culture.

The subject matter disclosed herein relates to a cell population containing mammalian retinal progenitor cells that are isolated according to a defined cell culture method and which express characteristic markers. The cell population may be a culture of cells isolated from a mammal and grown in vitro. For example, the culture may include a suspension of cells or adherent cells cultured in a culture plate, dish, flask, or bioreactor. The sample may be homogeneous or heterogeneous, which may be determined by expression of one or more markers as defined herein. The cell population disclosed herein is a mixed cell population and may contain a mixture of undifferentiated and differentiated cells. Relative expression levels of markers characteristic of the retinal progenitor cells defined herein may vary between cells within the population.

Retinal progenitor cells may be characterized by their expression of molecular markers, including cell surface markers and non-surface ("genetic") markers. While it is common in the art to refer to cells as "positive" or "negative" for a particular marker, actual expression levels are a quantitatively determined. The number of molecules on the cell surface (or located elsewhere) can vary by several logs, yet still be characterized as "positive". It is also understood by those of skill in the art that a cell which is negative for staining, i.e. the level of binding of a marker specific reagent is not detectably different from a control, e.g. an isotype matched control, may express minor amounts of the marker. Characterization of the level of labeling ("staining") permits subtle distinctions between cell populations. The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

To normalize the distribution to a control, each cell is recorded as a data point having a particular intensity of staining. These data points may be displayed according to a log scale, where the unit of measure is arbitrary staining intensity. By way of example, the brightest stained cells in a sample can be as much as 4 logs more intense than unstained cells. When displayed in this manner, cells falling in the highest log of staining intensity are bright, while those in the lowest intensity are negative. The "low" positively stained cells have a level of staining above the brightness of an isotype matched control, but are not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Expression of markers may be subject to change during culture of retinal tissue from which the retinal progenitor cells and cell populations are derived. For example, differences in marker expression can be influenced by culture conditions such as oxygen levels (i.e., atmospheric oxygen conditions, or "normoxic" conditions; or low oxygen conditions, also known as "hypoxic" conditions). By way of non-limiting example, the low oxygen conditions may include 0.5%-10% oxygen (i.e., 0.5, 1, 1.5, 2, 2.5, 3, 3.5, 4, 4.5, 5, 5.5, 6, 6.5, 7, 7.5, 8, 8.5, 9, 9.5, or 10%). Those of ordinary skill in the art will be aware that marker expression of the retinal progenitor cells and cell populations is not static and may change as a function of one or more culture conditions, i.e., culture media, oxygen levels, number of passages, time in culture, etc.

Retinal progenitor cells and cell populations may express one or more, two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, twenty or more, twenty-five or more, thirty or more of the markers defined herein, or any increment in between up to fifty or more markers.

By way of non-limiting example, retinal progenitor cells and cell populations containing retinal progenitor cells are characterized or screened by expression of one or more markers such as, e.g., nestin, vimentin, Sox2, Ki67, MHC Class I, Fas/CD95, MAP2, CD9, CD81, AQP4, CXCR4, CD15/LeX/SSEA1, GD2 ganglioside, CD133, P3-tubulin, GFAP, OPN/SPP1, basic fibroblast growth (bFGF), PTN, KDR, and/or TEK. In certain embodiments, the retinal progenitor cells and cell populations express one or more markers selected from the group consisting of nestin, Sox2, Ki-67, MHC Class I, and Fas/CD95, wherein nestin is expressed by greater than 90%, or 95-99% (i.e., 95, 96, 97, 98, or 99%) of the cells in the population, wherein Sox2 is expressed by greater than 80%, or 90-99% (i.e., 90, 91, 92, 93, 94, 95, 96, 97, 98, or 99%) of the cells in the population, wherein Ki-67 is expressed by greater than 30%, or 40-60% (i.e., 40, 41, 42, 43, 44, 45, 46, 46, 48, 49, 50, 51, 52, 53, 54, 55, 56, 57, 58, 59, or 60%)) of the cells in the population (i.e., 60-85% (i.e., 60, 61, 62, 63, 64, 65, 66, 67, 68, 69, 70, 71, 72, 73, 74, 75, 76, 77, 78, 79, 80, 81, 82, 83, 84, or 85%) of cells grown under normoxic/atmospheric oxygen conditions, 80-90% (i.e., 80, 81, 82, 83, 84, 85, 86, 87, 88, 89, or 90%) of cells grown under hypoxic conditions), wherein MHC Class I is expressed by greater than 70%, or 90% of the cells in the population, wherein osteopontin (OPN) is expressed in an amount greater than 20 ng/$10^6$ cells/24 hours by the cells in the population, wherein basic fibroblast growth factor (bFGF) is expressed in an amount approximately 50-300 pg/$10^6$ cells/hour (i.e., 50, 55, 60, 65, 70, 75, 80, 85, 90, 95, 100, 105, 110, 115, 120, 125, 130, 135, 140, 145, 150, 155, 160, 165 170, 175, 180, 185, 190, 195, 200, 205, 210, 215,220, 225, 230, 235, 240, 245, 250, 255, 260, 265, 270, 275, 280, 285, 290, 295, or 300 pg/$10^6$ cells/hour) by the cells in the population, when the cells are present in a carrier that did not include bFGF at baseline, and/or wherein Fas/CD95 is expressed by greater than 30%, or 40-70% (i.e., 40, 41, 42, 43, 44, 45, 46, 46, 48, 49, 50, 51, 52, 53, 54, 55, 56, 57, 58, 59, 60, 61, 62, 63, 64, 65, 66, 67, 68, 69, or 70%) of the cells in the population. The cells in the population may additionally express mesencephalic astrocyte-derived neurotrophic factor (MANF) (e.g., in an amount between about 0.5 and about 2.5 ng/$10^6$ cells/24 hours (i.e., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 ng/$10^6$ cells/24 hours)), pigment epithelium-derived growth factor (PEDF) (e.g., in an amount up to about 30 ng/$10^6$ cells/24 hours (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 ng/$10^6$ cells/24 hours)), pleiotrophin (PTN) (e.g., in an amount between about 50 and about 600 pg/$10^6$ cells/24 hours (e.g., 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, or 600 pg/$10^6$ cells/24 hours)); and/or midkine (MDK) (e.g., in an amount up to about 12 ng/$10^6$ cells/24 hours (e.g., 1, 2, 3, 4, 5, 6, 7, 8, 9, 10, 11, or 12 ng/$10^6$ cells/24 hours)).

The retinal progenitor cells and cell populations may additionally (or alternatively) further express one or more markers selected from the group consisting of vimentin, CD9, CD81, AQP4, CXCR4, CD15/LexA/SSEA1, GD2 ganglioside, CD133, P3-tubulin, MAP2, GFAP, OPN/SPP1, PTN, KDR, and/or TEK. GFAP may be expressed by 5-10% of the cells in the population. In some embodiments, MHC Class II, which is related to immune tolerance of an allogenic product may be expressed by 1-3% (i.e., 1, 2, or 3%) or by less than 2% of the cells in the population. CXCR4 may be expressed by 5-30% (i.e., 5, 6, 7, 8, 9, 10, 11, 12, 13, 14, 15, 16, 17, 18, 19, 20, 21, 22, 23, 24, 25, 26, 27, 28, 29, or 30%) of cells grown under atmospheric oxygen conditions, but 90% of cells grown under hypoxic conditions. CD15 may be expressed by 4-35% (i.e., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35%) of cells in the population, i.e., 4-8% (i.e., 4, 5, 6, 7, or 8%) of cells grown under atmospheric oxygen conditions, at 15-35% (i.e., 15, 16, 17, 18, 19, 20, 21, 22, 23, 24, 25, 26, 27, 28, 29, 30, 31, 32, 33, 34, or 35%) of cells grown under hypoxic conditions. GD2 may be expressed by 2-15% (i.e., 2, 3, 4, 5, 6, 7, 8, 9, 10, 11, 12, 13, 14, or 15%) of cells in the population, i.e., 2-4% (i.e., 2, 3, or 4%) of cells grown under atmospheric oxygen conditions, 15% of cells grown under hypoxic conditions.

Osteopontin (OPN) is a candidate potency marker for the cells and cell populations described herein. ELISA results have demonstrated that OPN is expressed by the cells and cell populations described herein in an amount >20ng/$10^6$ cells/24 hours.

In alternative embodiments retinal progenitor cells and cell populations are characterized or screened for low, trace, negative, or decreased expression of one or more of ABCA4, AIPL1, AKT3, APC2, BSN, CCNG2CDHR1, CRX, CD24, Claudin 11, CNTF, CNTFR, DACH1, DAPL1, DCX, DLG2 and 4, DLL4, EPHA7, EYS, FLT1, FSTL5, FZD5, FGF9, 10, and 14, GADD45G, GRIA2, HES5 and 6, HEY2, HEYL, HGF, HIF3A, IMPG1 and 2, JAK2 and 3, KLF4, MAP6, myelin basic protein (MBP), MYCN, Nanog, NBL1, NEFL, NEFM, NEUROD1, NEUROD4, NEUROG1, NEUROG2, NOTCH 1, 2, and 3, NRL, NRCAM, NRSN, NRXN1, 2, and 3, OCT4, OLIG2, OPN1MW1 and 2, OPN1SW, OTX2, PAR4, PAX6, PRPH2, RAX1 and 2, RBP3, RCVRN, RELN, RGR, rhodopsin, RICTOR, RP1, RRH, RXRG, SIX3 and 6, SOX 8, SLC25A27, STAT1, STAT3, SYP, SYT4, WIF1, VSX2, and/or VSX1 and 2. The expression pattern of these markers may be used to distinguish retinal progenitor cells or cell populations from tissues of origin, e.g., freshly isolated retinal tissues.

Other markers whose expression may be increased relative to tissues of origin include, without limitation, ADM, ANGPT1, ANGPTL2 and 4, ATP5D, BHLHE40, CCL2, CCNB1, CCND2, and CCNDE1, CD44, CDKN2A, Claudin 1, 4, and 6, CPA4, CTGF, CXCL12, DKK2, EMP1, FOXC2, FZD6, GADD45B, HES1, HIF1A, HOXB4, IGF1, IGFBP3, 5, and 7, IL1A, IL1R, IL1RAP, IL4R, IL7R, IL11, IL18, JAG1, LIF, LOX, BDNF, EGF, EGFR, FGF1, 2, 5, and 9, KLF4, 5 and 12, MITF, MMP1, MYC, NCAN, NEFH, NOG, NTF3, NTRK2, NRP1 and 2, OSMR (IL31RA), OTX1, PAX8, PDGFA, B, and C, PLAU, PRRX1, RPE65, SDF-1, SFRP1 and 4, SIX1 and 4, SLC25A1, 19, and 20, TEK/TIE1, THBS1 and 2, TLR4, VEGFA, VEGFC WNT5A, and/or WNT7B.

Retinal progenitor cells and cell populations are distinguished from other central nervous system progenitor cell types like brain progenitor cells and neural stem cells, and others which may be derived from fetal CNS tissues such as brain and spinal cord. Markers that may be increased relative to other CNS progenitor cells include, without limitation, ARR3 (arrestin C), CDF10, CDKN2A, CTGF, CXCL12/SDF1, BHLHE41, BMP2, DKK1, EGFR, EPHB2, FN1, FOSL1 and 2, FOXD1, GABBR1, GAS1 and 6, GBX2, HHEX, HOXB2, IGFBPS and 7, INHBA, JAG1, KDR, KLF10LHX9, LHX2, LIF, MET, NEUROD1, NTF3, NTRK2, OPTN (optineurin), RCVRN, SAG (S-arrestin), SERPINF1 (PEDF), SFRP1, SOX3, TBX3, TGFB, WIF, WNT5A, and/or WNT5B. Markers that may be decreased relative to other CNS progenitor cells include, without limitation, AQP4, ASLL1, CLDN11, CDKN1B, CCL2, CCNG2, CXCR4 (SDF1 receptor), DCX, DLX2 and 5, EMX2, EPHA3, 4, and 7, FABP7, FOXG1, GRIA 1, 2, and 3, HGF, IL2, KLF4, LIFR, MNX1, NGF, NKX2-2, NOTCHI, NPY, NPY2R, OLIG2, OMG, PBX1, PDGFRA, RTN1, SCGN, SOX11, TFAP2B, TNFRSF21, and/or WNT7A.

Donor cells can be cultured without antibiotics in order to avoid altering cells. Moreover, without antibiotics, use of very low passage cells is possible since occult microbial contamination can be ruled out. Preferably, use of low passage cells has a low risk of transformation and/or tumor formation. Additionally, use of low passage cells are closest to the natural cells present in the developing retina.

Any suitable basal media can be used for growth and culture of RPCs. Cell culture describes a process by which cells are grown under controlled conditions, generally outside of their natural environment. Cell populations can be grown or cultured in any cell culture medium known in the art. In alternative embodiments the term "basal medium" refers to any medium that can support cell growth. The basal medium provides standard inorganic salts such as zinc, iron, magnesium, calcium, and potassium, vitamins, glucose, buffer system, and key amino acids. The basal medium that can be used in the present invention includes, but is not limited to, Minimum Essential Medium Eagle, ADC-1, LPM (Bovine Serum Albumin-free), F10 (Ham), F12 (Ham), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153, and ULTRACULTURE™. Preferred media for use in culturing the retinal progenitor cells disclosed herein are Advanced DMEM/F12 and ULTRACULTURE™. A number of these media are summarized in Methods in Enzymology, Volume LVIII, "Cell Culture," pp. 62-72.

In alternative embodiments "conditioned medium" refers to a medium that is altered as compared to a base or basal medium. For example, the conditioning of a medium may cause molecules, such as nutrients and/or growth factors, to be added to or depleted from the original levels found in the base medium. A medium can be conditioned by allowing cells of certain types to be grown or maintained in the medium under certain conditions for a certain period of time. For example, a medium can be conditioned by allowing retinal progenitor cells to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

Examples of cell culture supplements or additives include, without limitation, ingredients to replace partly or wholly the role of serum in supporting cell survival or growth. For example, supplements may include insulin, transmetalloproteins, trace elements, vitamins, or other factors. These factors are generally not included in the basal medium but are provided by serum used generally in culturing cells. The supplement or additive may include at least one or more of the following components that support cell growth: one or more insulins or replacements thereof, one or more transmetalloproteins or replacements thereof, one or more trace elements (e.g., selenium, iron, zinc, copper, cobalt, chromium, iodine, fluoride, manganese, molybdenum, vanadium, nickel, tin), one or more vitamins (e.g., Vitamin C, Vitamin E, Vitamin A, Vitamin B-group), one or more salts (e.g., sodium salts, magnesium salts, calcium salts, or phosphate salts), one or more buffers (e.g., phosphate buffered saline, HEPES buffer), one or more amino acids (e.g., L-glutamine), one or more hormones, hormone-like compounds or growth factors (such as, e.g., transferrin, EGF, NGF, ECGF, PDGF, FGF, IGF, LIF, interleukins, interferons, TGF, and/or VEGF, glucagon, corticosteroids, vasopressin, prostaglandins), serum albumin or replacements thereof, one or more carbohydrates (glucose, galactose, fructose, mannose, ribose, glycolytic metabolites), one or more antibiotics and/or antimycotics (e.g., penicillin, streptomycin, Fungizone), and one or more lipids (e.g., free and protein-bound fatty acids, triglycerides, phospholipids, cholesterol, ethanolamine). Many commercialized serum replacement additives, such as KNOCKOUT SERUM REPLACEMENT™ (KOSR), N2, B27, STEMPRO™, Insulin-Transferrin-Selenium Supplement (ITS), and G5 are well known and are readily available to those skilled in the art. These additives are characterized by well-defined ingredients, so the concentrations of its components can be determined based on its proportion in the medium.

By way of non-limiting example, the cells and/or small cellular clusters are cultured in a sterile environment containing serum-free media or serum-containing media, and antibiotics and antifungals or no antibiotics or anti-fungals, for no more than about 1, 2, 3, 4, 5, 6, 7, 8, 9 or 10 or more passages. The cells and/or and small cellular clusters are cultured in a basal culture media (e.g., Dulbecco's Modified Eagle Medium: Nutrient Mixture F-12™ (DMEM/F12™) media or an ADVANCED DMEM/F12™ media (Gibco-Invitrogen-Life Technologies, Carlsbad Calif.)) or an ULTRACULTURE™ media (BioWhittaker-Lonza Walkersville, Inc., Walkersville, Md.), optionally together with N2 supplement (Invitrogen) or B27 or B27 XENO FREE™ (Invitrogen), L-glutamine or GLUTAMAX™ (Invitrogen), and human recombinant growth factors including, for example, of EGF and bFGF (Invitrogen), or other growth factors. For example, the DMEM/F12™ media is used for human cells and the ULTRACULTURE™ media is used for feline or canine cells.

In alternative embodiments, additionally (or alternatively), vitamin C can be included in the culture media. For example, between about 0.1 mg/ml or 0.05 mg/ml, or between about 0.01 mg/ml to about 0.5 mg/ml (e.g., 0.01, 0.02, 0.03, 0.04, 0.05, 0.06, 0.07, 0.08, 0.09, 0.10, 0.11, 0.12 0.13. 0.14. 0.15, 0.16, 0.17, 0.18, 0.19, 0.20, 0.21, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 039, 0.40, 0.41, 0.42, 0.43, 0.44, 0.45, 0.46, 0.47, 0.48, 0.49, or 0.5 mg/ml) can be included in the culture media changed every 1 or 2 days.

The culture media can also optionally be supplemented with albumin, or human or feline or canine albumin, or recombinant albumin, or albumin. By way of non-limiting example, albumin can be added in an amount to have an initial concentration of about 1.0 mg/ml.

Cultures of mammalian retinal progenitor cells can be produced in medium containing reduced serum or no serum. Examples of serum include fetal bovine serum, calf serum, newborn calf serum, goat serum, horse serum, human serum, rabbit serum, rat serum, mouse serum, among others. Under certain culture conditions, serum concentrations can range from about 0.05% v/v to about 20% v/v (e.g., 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 1, 1.5, 2, 2.5, 3, 3.5, 5, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20%). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, retinal progenitor cells and cell populations including retinal progenitor cells are grown without serum ("serum-free"), without serum replacement and/or without any supplement.

In alternative embodiments retinal progenitor cells or cell populations containing retinal progenitor cells are cultured under "xeno-free" conditions. "Xeno-free" or "xenogen-free" refers to conditions where cells of a certain species (e.g., human cells) are grown or cultured only in the presence of human products or supplements (e.g., human serum albumin, human serum), but not products from other species. This is particularly important for cells that are used for transplantation into a human. Cells that have been exposed to a variety of undefined animal-derived products make them undesirable for clinical applications, because of an increased risk of graft rejection, immunoreactions, and viral or bacterial infections, prions, and yet unidentified zoonoses. Moreover, for all mammalian uses, including human use or non-human mammalian uses (e.g., veterinary uses), cells are screened for normal karyotype or presence of infection or contamination, e.g., by mycoplasma, gram negative bacteria (e.g., endotoxin test), fungi and the like. Cells may also be screened for tumorigenicity or transformation to a cancerous phenotype by telomerase activity assay, hTERT gene expression, and growth in soft agar or tumor formation in nude mice. Such assays are known in the art and well within the purview of the skilled artisan.

Retinal progenitor cells or cell populations containing retinal progenitor cells may be cultured on feeder cell layers (e.g., embryonic or adult fibroblasts), or in the presence of an extracellular matrix scaffold or substrates such as collagen, entactin, heparin sulfate proteoglycans, fibronectin, laminin, gelatin, or MATRIGEL™. For example, PURECOL® collagen is known as the standard of all collagens for purity (>99.9% collagen content), functionality, and the most native-like collagen available. PURECOL® collagen is approximately 97% Type I collagen with the remainder being comprised of Type III collagen, and is ideal for coating of surfaces, providing preparation of thin layers for culturing cells, or use as a solid gel. Another example of a scaffold or substrate known in the art is CELLSTART™ (Invitrogen).

In some embodiments, cell culture conditions can involve growth of cells in an incubator set at 37° C., 5% C02. Retinal progenitor cells or cell populations containing retinal progenitor cells may be cultured under normoxic or atmospheric (20%), and can be grown under conditions that approximate oxygen levels of a developing fetal retina during gestation, i.e., "low" or "hypoxic" conditions, e.g., 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% oxygen, or any increment in between.

In alternative embodiments plating density refers to the number of cells per volume of culture medium or the number of cells per $cm^2$ in adherent culture. A similar term in this context is "confluence", which is commonly used as a measure of the number of the cells in a cell culture dish or a flask, and refers to the coverage of the dish or the flask by the cells. For example, 100 percent confluency means the dish is completely covered by the cells, and therefore no more room left for the cells to grow; whereas 50 percent confluency means roughly half of the dish is covered and there is still room for cells to grow.

Passaging (also known as subculture or splitting cells) involves transferring a small number of cells into a new vessel. Cells can be cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached. This is commonly done with a mixture of an enzyme such as trypsin-EDTA or non-enzymatic solution like Cell Dissociation Buffer; however, a variety of enzyme or non-enzyme mixes or preparations are available for this purpose. A small number of detached cells can then be used to seed a new culture.

Most primary cell cultures have limited lifespan and do not proliferate indefinitely. After a certain number of population doublings (called the Hayflick limit), cells undergo the process of senescence and stop dividing, while generally retaining viability. In some embodiments, the retinal progenitor cells and cell populations can be cultured for no more than 10 passages, for example, are passaged one, two, three, four, five, six, seven, eight, nine, or ten passages. In some embodiments, the RPCs are passaged about 4-6 (e.g., 4, 5, or 6) times under standard oxygen conditions and, optionally, subsequently cultured for about 1-10 (e.g., 1, 2, 3, 4, 5, 6, 7, 8, 9, or 10) passages under low oxygen conditions.

In alternative embodiments, cells can be passaged (in standard oxygen conditions, in low oxygen conditions, and/ or in any combinations thereof) more than 5 times, such as, e.g., six, seven, eight, nine, ten, eleven, twelve, thirteen, fourteen, fifteen, sixteen, seventeen, eighteen, nineteen, twenty or more passages. In certain embodiments, the retinal progenitor cells and cell populations are cultured for about 5-32 (e.g., 5, 6, 7, 8, 9, 10, 11, 12, 13, 14, 15, 16, 17, 18, 19, 20, 21, 22, 23, 24, 25, 26, 27, 28, 29, 30, 31 or 32) passages. Those skilled in the art will recognize that other methods known in the art may be used to culture the cells for more than 32 passages (i.e., 33, 34, 35, 36, 37, 38, 39, 40, 41, 42, 43, 44, 45, 46, 47, 48, 49, 50, or more passages).

In various embodiments, the sample of cells is screened for the presence of a pathogen, a bacteria, an endotoxin, a fungus, a mycoplasma, a virus, a hepatitis virus or an HIV virus. The sample of cells can also be screened for the presence of a normal karyotype; viability; and/or tumorigenicity. Optionally, the sample of cells does not exhibit elevated telomerase activity.

In any of these methods as provided herein, retinal cells and/or retinal tissue can be frozen either before or after isolation, selection, and/or culture. Cell freezing can be accomplished using any cryopreservation agents and/or techniques commonly used in the art. Frozen cells can be thawed prior to use using any protocol known in the art.

The viability of cells can be examined prior to their use in any of the methods described herein. By way of non-limiting example, prior to cryopreservation, preferably at least 70% (i.e., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Following thawing, preferably at least 70% (i.e., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Similarly, upon cell culture recovery, preferably at least 70% (i.e., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Determination of the number of viable cells at any stage is within the routine level of skill in the art.

In certain embodiments, the final product formulation has been shown to retain optimal viability (i.e., at least 85%) for up to 4 hours or more (e.g., 4, 5, 6, 7, 8, 9, 10, 11, 12, 13, 14, 15, 16, 17, 18, 19, 20, 21, 22, 23, 24, or more) when kept on ice (i.e., at 0-4° C.). This, in turn, will allow local transportation of the cell preparation to regional clinical sites.

Further expansion of cells under low oxygen conditions can be used to greatly enhance the cell yield per donation. For example, in some embodiments, cells may be passaged 5-12 (i.e., 5, 6, 7, 8, 9, 10, 11 or 12) or more times total. By way of non-limiting example, in one embodiment, this may include a secondary low oxygen expansion of 3-6 passages (i.e., 3, 4, 5, or 6) that occurs after 4-6 passages (i.e., 4, 5, or 6) in standard oxygen conditions. However, those skilled in the art will recognize that the total number of passages may be about 1-32 or more passages (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 32 or more), and this may include a secondary low oxygen expansion of 1-20 or more passages (e.g., 1, 2, 3, 4, 5, 6, 7, 8, 9, 10, 11, 12, 13, 14, 15, 16, 17, 18, 19, or 20 or more). Determination of the appropriate number of total passages as well as the number of low oxygen passages is within the routine level of skill in the art. Use of this secondary low oxygen culture passages greatly expand yield from a working bank of GMP hRPCs (such as those that have are derived by culturing under standard oxygen conditions). For example, cells from the standard normal oxygen bank can be thawed and further expanded for an additional 1-20 (e.g., 1, 2, 3, 4, 5, 6, 7, 8, 9, 10, 11, 12, 13, 14, 15, 16, 17, 18, 19, or 20) passages under low oxygen conditions.

While the use of fewer low oxygen cell passages is possible, the resulting yield would likely be lower. Moreover, while the use of more low oxygen cell passages is also possible, this would potentially have an increased risk of the resulting product being faulty due to potential phenotypic drift with loss of efficacy and/or accumulation of undesired genetic abnormalities.

Following the secondary low oxygen culture passages, in some embodiments, the retinal progenitor cells undergo a "recovery period" in which they are allowed to grow under standard oxygen conditions for a short period of time between 1 hour and up to 5 days (i.e., 1, 2, 3, 4, 5, 6, 7, 8, 9, 10, 11, 12, 13, 14, 15, 16, 17, 18, 19, 20, 21, 22, 23, 24, 24, 36, 48, 60, 72, 84, 96, 108, or 120 hours). In alternative embodiments, during this recovery period, the cells are allowed to growth without undergoing any further passaging.

Accordingly, in one non-limiting example, retinal progenitor cells for use in any of the compositions and methods described herein may be produced using a "hybrid" approach involving (a) culture under standard oxygen conditions for a number of passages followed by (b) culture under low oxygen conditions for a number of passages, optionally followed by (c) culture under standard oxygen conditions for a set period of time without any further passaging. Determination of the appropriate number passages under standard oxygen conditions and/or low oxygen conditions as well as the appropriate duration of the recovery period is within the routine level of skill in the art.

The resulting cell product produced using this new culture methodology has been tested in vitro and in animals, and results similar to those with cell product that did not undergo the secondary low oxygen culture have been observed.

Those skilled in the art will recognize that the addition of this secondary low oxygen component to the overall process is conducive to automated manufacturing methods in that complex procedures such as initial dissection and plating are not needed and the passaging done will be quite standardized with cells that are strongly proliferating.

RPCs can additionally be generated through induced pluripotent stem cell (iPS) conversion of existing RPCs followed by expansion in a more primitive, proliferative state. The iPS can then be re-differentiation back to RPCs using any method(s) known in the art. In this scenario, the previous epigenetic imprinting conferred as RPCs helps to redirect the cells back to their original state, thereby increasing RPC yield and/or promoting safety of a high yield allogeneic product (i.e., by avoiding contamination with pluripotent cells). This expansion methodology could provide a very large and potentially infinite (non-senescing)

source of RPCs, derived from clinically proven RPC samples, without the need for repeated fetal tissue procurement.

RPCs can additionally be manufactured from a pluripotent cell line, either one such line derived from RPCs, as above, or not. Such a derivation could include partial differentiation into "embryoid bodies" containing primitive retinal structures, i.e., eye cup derivatives, from which RPCs could be harvested, purified, and further expanded.

In alternative embodiments similar methods can be performed using autologous cells where donor cells for iPS are obtained from ciliary body epithelium or from iris, as both of these tissues are accessible to the surgeon and have developmental imprinting that overlaps with (although not exactly the same as) the retina.

Administration of RPCs and Methods of Treatment

Also provided herein are methods and uses of cultured retinal progenitor cells prepared as a cell suspension and used as allogeneic grafts for treatment of patients with retinal disease. For example, provided herein are cell-based therapies comprising or consisting of use of cultured heterogeneous cell populations from an immature mammalian, e.g., human retina.

Cell populations and related compositions described herein may be provided to a subject or patient by a variety of different means. By way of non-limiting example, they can be provided locally, e.g., to a site of actual or potential injury or disease. In some embodiment, they are provided using a syringe or needle to inject the compositions at a site of possible or actual injury or disease. In other embodiments, they are provided systemically, i.e., administered to the bloodstream intravenously or intra-arterially. The particular route of administration will depend, in large part, upon the location and nature of the disease or injury being treated or prevented. Accordingly, in alternative embodiments the methods described herein include providing a cell population or composition via any known and available method or route, including but not limited to intraocular, oral, parenteral, intravenous, intra-arterial, intranasal, and intramuscular administration.

The determination of suitable dosages and treatment regimens may be readily accomplished based upon information generally known in the art and obtained by a physician.

By way of non-limiting example, in alternative embodiments the cell dose may be between about 0.3 and about 0.5 million cells (e.g., 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 million cells) or between 0.5-3 million cells (e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3 million cells).

The efficacy results observed between both dose ranges are roughly similar. However, there is a possible increased risk with larger doses (e.g., 2-3 million cells) of the cells persisting in the visual axis, sticking to posterior lens capsule, and/or entering anterior chamber (pseudo-hypopyon) if the patient's eye has weakened zonules. Moreover, those skilled in the art will recognize that it is possible that the duration of graft survival might be proportional to dose and, thus, the original graft size.

Dosing frequency of allogeneic hRPCs in the vitreous cavity will be important. In various embodiments, subsequent doses (i.e., "redoses") can be made to the same eye of the patient or to the fellow eye. Redosing the fellow eye in both animal models as well as a number of patients has been performed without subsequent immune sequelae, thereby suggesting the redosing will be well-tolerated bilaterally (and, presumably, in the same eye, as has been performed in animals up to 3 times).

Grafts can survive in patients with RP for a year or more. However, as they tend to disappear from the vitreous after approximately 1-1.5 years, this suggests that redosing within approximately a 1 to 2 year time frame might not be too aggressive and, in fact, may become the future norm in a majority of cases.

In any of the methods disclosed herein, treatment may involve a single treatment or multiple (e.g., 2, 3, 4, 5, 6, 7, 8 or 9 or more) treatments. For preventative purposes, it is contemplated in certain embodiments that purified cell populations are administered following a stress that might potentially cause retinal injury.

In one embodiment, the cell populations and compositions may be locally administered as a single injection to the vitreous cavity or subretinal space of the subject.

While the compositions and methods described herein are not limited by any particular mechanism of action, an exemplary mechanism of action is diffusible and/or trophic. Evidence is consistent with concept of trophic reprogramming of moribund host cones, resulting in switch from apoptotic trajectory to regeneration of photic processing capability. This can be direct or indirect. Involvement of other ocular tissues not ruled out. This mechanism allows for placement of a graft of a heterogeneous mixture of fetal neural retinal cells in a vitreous or a subretinal space.

In alternative embodiments vitreal placement enhances diffusion-based treatment effect. This mechanism can allow a graft of heterogeneous mixtures of fetal neural retinal cells to be placed out of the visual axis, yet still treat patient's macula. Moreover, a vitreal placement is used to greatly simplify a treatment, as this exemplary treatment can increase availability to needy patients worldwide. Additionally, vitreal placement may aid in immune tolerance by being remote to vasculature. Those skilled in the art will recognize that vitreal placement avoids potential complications of subretinal surgery, avoids risks of general anesthesia, does not require that a hole (retinotomy) be made in retina (which raises risk of retinal detachment, bleeding), and/or does not require the patient's retina undergo a focal detachment (focal detachment can lead to photoreceptor damage or loss, retinal tears, bleeding, global retinal detachment and, in RP, detachment of the thin, atrophic, and adherent retina will be a difficult/risky procedure).

In some embodiments, the cells are placed in the vitreous cavity using a suitable needle size and length. In alternative embodiments, the syringe has a minimal (i.e., 1 microliter) dead space, in order to enhance the efficiency of delivery and avoid loss of product due to retention in the syringe. The use of a short needle (e.g., 31G (gauge) with 5/16 inch length or 30G with a ½ inch length) allows for maximum convenience (i.e., suitability for use in a clinical or office setting). However, the use of a longer needle length (e.g., 27G or 25G with a 5/8 inch length) allows for optimum placement (used under operating scope) further back (posterior) in the vitreous, closer to the macula. Determination of the appropriate needle size and length is within the routine level of skill in the art. When choosing the appropriate needle size and length, it is important that cell viability remain above the requisite threshold value after cells were passed through needle.

In alternative embodiments placement of the cells is within the anterior vitreous, which is simple and allows for maximum safety and convenience. In contrast, in alternative embodiments, placement is in the posterior vitreous (near the posterior pole), which requires direct visualization of needle tip to avoid penetrating injury of retina. However, this may enhance the overall treatment effect and may represent the optimal placement and efficacy.

While retinal cell replacement is possible, it is not required for clinical efficacy. Likewise, donor cell migration into retina is possible but is not required for clinical efficacy; donor cell integration in retinal circuitry is possible but is not required for efficacy; donor cell integration into the outer nuclear layer/macula of host retina is possible but is not required for efficacy; and/or donor cell integration into retina is possible but is not required for sustained graft survival.

In some embodiments, the RPC cells can be injected in a vitreous cavity where, optionally, no vitrectomy or subretinal surgery is required. However, some embodiments may involve the optional use of one or more of vitrectomy, core vitrectomy, and/or a vitreolytic agent to remove vitreous gel and optimize mobility and penetration of injected cells to the posterior vitreous (e.g., the optimal location in proximity to posterior pole of eye). In some cases, use of surgical vitrectomy may enhance placement of cells in the eye.

The cells can also be implanted into (e.g., injected into) a subretinal space, or, they can be implanted into (e.g., injected into) an eye using any standard intraocular injection procedure, e.g., using a hypodermic or an angled insertion pathway. In some embodiments, no retinotomy or no intraocular gas or silicon oil is required.

Alternatively, an anterior chamber paracentesis can optionally be performed, depending on situation, as determined by one of skill in the art. In some embodiments, no suturing of globe is needed during and/or after a procedure.

Any of the methods disclosed herein may include the step of administering the compositions under topical anesthesia directly to the vitreous cavity, without need for systemic immune suppression of the subject. Additionally, while tissue typing of graft and matching to patient or subject is not required, it may be performed if desired, for example using any tissue typing and matching techniques known to those skilled in the art.

As noted, in any of the methods described herein, in alternative embodiments, only topical anesthesia is used, e.g., no local, regional, general anesthesia used. However, in some cases, local, regional or general anesthesia may additionally or alternatively be used during administration. Examples of suitable local anesthetics suitable for use in the methods disclosed herein include, without limitation, mepricaine, proparacaine, prilocaine, ropivacaine, benzocaine, bupivacaine, butamben picrate, chlorprocaine, cocaine, dibucaine, dimethisoquin, dyclonine, etidocaine, hexylcaine, ketamine, lidocaine, mepivacaine, pramoxine, procaine, tetracaine, salicylates and derivatives, esters, salts and mixtures thereof.

In certain embodiments, no anti-inflammatory and/or immune suppression (i.e., systemic immune suppression) is required. Moreover, clinical experience supports that none is needed, as, in some cases, graft survival can be seen over many months, for example, including and exceeding 1 year.

However, if necessary, anti-inflammatory and/or immune suppression therapy as post-operative drops can be included. For example, patients may be treated post-injection with topical steroid eye drops, with administration tapering over 1 week, or, alternatively, after up to 2 weeks, if indicated clinically for evidence of persistent post-treatment inflammation.

In alternative embodiments, there is no mandatory bed rest, post-op and/or need for "face-down" positioning. These methods can be performed an outpatient procedure and, likely do not require any overnight hospital stay.

In some embodiments, during administration, the patient's head is tilted back from reclined seated position, as close to horizontal as possible, in order to maximize settling of injected cells within the vitreous gel towards the posterior pole of eye, which is the most important part of retina for vision. Patients should maintain this position for approximately 30 minutes or more, as tolerated by patient. In addition, following administration, patients should also spend time laying on back, looking up, at home.

In alternative embodiments any of the compositions and methods described herein involving or using heterogeneous mixtures of fetal neural retinal cells (e.g., retinal progenitor cells) are used for treating, ameliorating, reducing the symptoms of, slowing the progress of, or preventing a retinal disease or condition, e.g., Usher's disease, retinitis pigmentosa (RP), a degenerative retinal disease, an age related macular degeneration (AMD), a wet AMD or a dry AMD, geographic atrophy, a retinal photoreceptor disease, a diabetic retinopathy, cystoid macular edema, uveitis, a retinal detachment, a retinal injury, macular holes, macular telangiectasia, a traumatic or an iatrogenic retinal injury, a ganglion cell or optic nerve cell disease, a glaucoma or an optic neuropathy, an ischemic retinal disease such as retinopathy of prematurity, retinal vascular occlusion, or ischemic optic neuropathy; or improving a photopic (day light) vision; or for improving correcting visual acuity, or improving macular function, or improving a visual field, or improving scotopic (night) vision.

Likewise, in alternative embodiments any of the compositions or methods described herein can be used to provide a rapid effect, increased best-corrected visual acuity, improved macular function, and/or the possibility of preserving or regaining central fixation.

In alternative embodiments using or practicing any of the compositions and methods disclosed herein results in various systemic benefits, e.g., changes in appearance in treated individuals possibly due to somatic improvements, which could be related to effect of light on circadian rhythms, pituitary function, release of hormones, vascular tone, etc.; improved sense of visual capabilities; improved ambulatory independence; improved sense of well-being; and/or improved activities of daily living.

Preferably, using or practicing any of the compositions and methods disclosed herein does not result in development of unwanted cell growth, e.g., tumors; infections, e.g., no endopthalmitis—a risk for any intraocular procedure; transmission of disease (however, prion or mad cow disease may be difficult to rule out); uveitis and/or acute graft rejection; elevated intraocular pressure; angle closure; hypotony; retinal detachment; and/or neovascularization.

In alternative embodiments the uses and methods described herein can rapidly and sustainably restore and/or preserve clinically significant degrees of visual function in a retina in mammalian (e.g. human) subjects, including but not limited to, improved photopic (day light) vision, increased best-corrected visual acuity, improved macular function, preserving or regaining central fixation, improved visual field, improvements in scotopic (night) vision, increased or improved sensitivity to sound, and improvements in visual acuity in a contralateral eye. Other changes may include various systemic benefits, e.g., changes in appearance due to somatic improvements, which could be related to effect of light on circadian rhythms, pituitary function, release of hormones, vascular tone; an improved sense of visual capabilities; improved ambulatory independence; improved sense of well-being; and/or improved activities of daily living. Such changes in vision can be measured by methods known in the art.

Visual benefits may be rapid and may occur within first week post-treatment, but may also occur as incremental benefits over longer periods of time. Retinal cell replacement and/or donor cell migration into the retina, retinal circuitry, or outer nuclear layer or macula may occur, but is not required for clinical efficacy; donor cell migration into retina is possible, but not required for clinical efficacy.

Measuring changes in vision, including improvements in vision resulting from treatment with the retinal progenitor cell compositions disclosed herein can be achieved using standard ophthalmic examination techniques, including but not limited to, fundus examination, best corrected visual acuity (BCVA), IOP, slit lamp examination, fluorescein angiography (FA), Optical Coherence Tomography (OCT), stereo-fundus photography, electroretinography (ERG), cone flicker electroretinography, perimetry (visual field), microperimetry, dark adaptation, maze negotiating skill, optokinetic/optomotor responses, pupillary responses, visual evoked potentials (VIP), and adaptive optics scanning laser ophthalmoscopy (AOSLO).

In vivo animal data has also suggested that intravitreal RPCs are a means of influencing multiple cell types in the diseased retina, including, but not limited to, Mueller cells (enhanced activation in retinal degeneration and/or increased local expression of glutamine synthetase (GS)); vascular compartment in diabetic retinopathy (less vascular permeability (leakage) and/or less ischemia based on decreased intra-retinal VEGF levels); enhanced recruitment of macrophages in retinal degeneration; increased local expression of bFGF (neurotrophic factor) in retinal degeneration; decreases expression of caspase 3 is decreased (indicating less retinal cell death). Thus, administration of RPCs could also be useful in a range of other retinal diseases, disorders, and conditions.

In addition, preliminary evidence of a crossover treatment effect in terms of indications of efficacy in the un-injected fellow eye has been observed. Specifically, this was seen in RCS rats (histological rescue of photoreceptors as well as ERG recordings) and also in a subset of patients (visual acuity testing), and it appears to be evidence of a "humoral" treatment effect that can extend beyond the confines of the injected eye. It is possible that this effect might be the result of the diffusion of cytokines and/or exosomes through the blood circulation, immune modulation, or both.

Likewise, in vivo data in animals suggests that a single intravitreal injection of osteopontin protein (OPN) alone replicates some, but not all, of the treatment effect provided by hRPCs. However, the effects of a single dose of pleiotrophin (PTN) and/or midkine differed from those observed with OPN in terms of timing and specific responses of the retinal cell populations.

In vivo data in animals also suggests that a single intravitreal injection of RPC-derived exosomes replicates, to some extent, the treatment effect provided by hRPCs.

Compositions and Formulations

In alternative embodiments the retinal progenitor cells and cell populations described herein may be formulated as a composition for administration by any or a variety of means including orally, parenterally, by inhalation spray, nasally, topically, intrathecally, intrathecally, intracerebrally, epidurally, intracranially or rectally. Compositions and formulations disclosed herein can contain pharmaceutically or veterinarily acceptable liquids, carriers, adjuvants and vehicles and can be in the form of liquids, tablets, capsules, implants, aerosols, gels, liposomes, nanoparticles and the like.

The retinal progenitor cells and cell populations may be administered to a subject in the form of pharmaceutical or veterinary compositions. In alternative embodiments the phrase "pharmaceutically acceptable" refers to molecular entities and compositions that do not produce adverse, allergic, or other untoward reactions when administered to an animal or a human. In alternative embodiments as used herein, "pharmaceutically acceptable carrier" includes any and all aqueous and nonaqueous carriers which includes water, ethanol, polyols (such as glycerol, propylene glycol, polyethylene glycol, and the like), and suitable mixtures thereof, vegetable oils, such as olive oil, and injectable organic esters, such as ethyl oleate.

The pharmaceutically acceptable carrier may optionally include albumin (e.g., human albumin), which is a protein that could improve cell survival within the preparation.

Likewise, any of the compositions or preparations disclosed herein may also include the excipient HYPOTHERMOSOL-FRS™ (HTS-FRS) (BioLife Solutions, Inc.), which is commercially-available hypothermic storage solution/formulation designed to mediate the level of post-storage necrosis and apoptosis in cells undergoing prolonged periods of hypothermic (2° C.-10° C.) preservation. (See, e.g., U.S. Pat. Nos. 6,921,633; 6,632,666; and WO 2005/009766).

In alternative embodiments the addition of albumin and/or HTS is used to extend the viability time for the retinal progenitor cells within any of the preparations disclosed herein up to about 24 hours (i.e., about 1, 2, 3, 4, 5, 6, 7, 8, 9, 10, 11, 12, 13, 14, 15, 16, 17, 18, 19, 20, 21, 22, 23, or 24 hours).

Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the presence of microorganisms may be ensured both by sterilization procedures and by the inclusion of various antibacterial and antifungal agents, for example, paraben, chlorobutanol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. It must be stable under the conditions of manufacture and storage and must be preserved against the contaminating action of microorganisms, such as bacteria and fungi. The use of such media and agents for pharmaceutically active substances is well known in the art.

An effective amount of the retinal progenitor cells or cell populations must be administered to the subject. In alternative embodiments an "effective amount" or "therapeutically effective amount" refers to the amount of the composition that produces a desired effect. An effective amount will depend, for example, in part, upon the molecule or agent delivered (here the retinal progenitor cells or cell populations), the indication for which the therapeutic agent is being used, the route of administration, and the size (body weight, body surface or organ size) and condition (the age and general health) of the subject or patient. Accordingly, the clinician or physician may titer the dosage and modify the route of administration to obtain the optimal therapeutic effect. An effective amount of a particular agent for a specific purpose can be determined using methods well known to those in the art. For any composition defined herein, the effective amount can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

Examples of effective amounts of the compositions described herein include cell suspensions at a volume of 5 µl, 10 µl, 15 µl, 20 µl, 25 µl, 50 µl, 100 µl, 150 µl, 200 µl, 250 µl, 300 µl, 350 µl, 400 µl, 450 µl, 500 µl or any increment in between up to 5000 µl (5 ml) (e.g., 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, or 5000 µl).

In alternative embodiments the lower and upper volume limits are limited by the delivery system and/or method. See, e.g., Kayikcuiglu, O. R. et al, (2006) Retina 26(9): 1089-90. For example, the upper volume limit when administered without vitrectomy is approximately 200 µl due to increased intraocular pressure. The upper volume limit when administered with vitrectomy into the vitreous cavity is limited by the volume of the vitreous cavity and can contain up to 5 ml or more. The upper limit for subretinal injection may be up to 200 µl due to retinal detachment. In alternative embodiments, these volumes include anywhere between 1000 to 10 million cells per dose, or 1000 to 2000 cells per dose, 2000 to 3000 cells per dose, 3000 to 4000 cells per dose, 400 to 5000 cells per dose, 5000 to 6000 cells per dose, 6000 to 7000 cells per dose, 7000 to 8000 cells per dose, 8000 to 9000 cells per dose, 9000 to 10,000 cells per dose, 10,000 to 15,000 cells per dose, 15,000 to 20,000 cells per dose, 20,000 to 25,000 cells per dose, 25,000 to 30,000 cells per dose, 30,000 to 35,000 cells per dose, 35,000 to 40,000 cells per dose, 40,000 to 45,000 cells per dose, 45,000 to 50,000 cells per dose, 50,000 to 55,000 cells per dose, 55,000 to 60,000 cells per dose, 60,000 to 65,000 cells per dose, 65,000 to 70,000 cells per dose, 70,000 to 75,000 cells per dose, 75,000 to 80,000 cells per dose, 80,000 to 85,000 cells per dose, 85,000 to 90,000 cells per dose, 90,000 to 95,000 cells per dose, 95,000 to 100,000 cells per dose, 100,000 to 125,000 cells per dose, 125,000 to 150,000 cells per dose, 150,000 to 200,000 cells per dose, 200,000 to 250,000 cells per dose, 250,000 to 300,000 cells per dose, 300,000 to 350,000 cells per dose, 350,000 to 400,000 cells per dose, 400,000 to 450,000 cells per dose, 450,000 to 500,000 cells per dose, 500,000 to 550,000 cells per dose, 550,000 to 600,000 cells per dose, 600,000 to 650,000 cells per dose, 650,000 to 700,000 cells per dose, 700,000 to 750,000 cells per dose, 750,000 to 800,000 cells per dose, 800,000 to 850,000 cells per dose, 850,000 to 900,000 cells per dose, 900,000 to 950,000 cells per dose, 950,000 to 1,000,000 cells per dose or in any increment in between 1000 cells and up to 10 million cells per dose. Dosages may, of course, vary according to frequency and duration of administration. In alternative embodiments the dosage of cells in the compositions described herein contains a high number of cells in a small, volume, such as, for example, 0.5 million cells per 100 µl. Cell numbers may be counted by any method known in the art, such as by hemacytometer, spectrophotometry, Coulter counter, flow cytometry, etc. Dosing may be administered once or may be administered over the course of several treatments.

Compositions can also be formulated for parenteral administration into the eye (particularly into the vitreous cavity or subretinal space), a vitreous cavity or a subretinal space, retina, brain, nerve or CNS by transscleral delivery, or by any method or protocol known in the art, e.g., including a transscleral delivery as described in U.S. Pat. No. 7,585,517; a sustained release delivery device for delivery to the interior of a patient's eye as described in U.S. Pat. No. 7,883,717; a device for insertion in the vitreous region of the eye as described in U.S. Pat. No. 5,378,475 or 5,466,233; or by use of a hypodermic syringe or angled insertion pathway, e.g., as described in U.S. Patent Application Publication Nos. 20110112470 or 20100256597 (describing a microneedle for targeted administration to a patient's eye); or via a hydrophilic polymer hydrogel with dimensions to pass through a puncta lacrimali e.g., as described in U.S. Patent Application Publication No. 20100209478; or a device that provides access to the sub-retinal space in a human eye e.g., as described in U.S. Patent Application Publication No. 20100191176. Anterior chamber paracentesis also can be performed as determined by one of skill in the art. Methods do not require suturing of globe during and/or after a procedure, particularly for intravitreal placement. However, this may be necessary for methods utilizing a vitrectomy procedure, for example, when placing cells in the subretinal space.

The compositions disclosed herein may also be formulated for intrathecal, intracerebral epidural, subcutaneous, intravenous, intramuscular and/or intraarterial administration; e.g., as described in U.S. Patent Application Publication No. 200500480021; by injection routes but also including a variety of infusion techniques. Administration may be carried out through the use of catheters or pumps, e.g., an intrathecal pump, or an implantable medical device. In alternative embodiments methods also may involve administration or transplantation of implants and artificial organs, bioreactor systems, cell culture systems, plates, dishes, tubes, bottles and flasks and the like, containing the retinal progenitor cells, cell populations, or compositions disclosed herein, such as those described in U.S. Pat. Nos. 7,388,042; 7,381,418; 7,379,765; 7,361,332; 7,351,423; 6,886,568; 5,270,192; and U.S. Patent Application Publication Nos. 20040127987; 20080119909; 20080118549; 20080020015; 20070254005; 20070059335; 20060128015.

In alternative embodiments the compositions containing retinal progenitor cells or cell populations are optionally be co-administered with one or more drugs. Non-limiting examples of drugs may include anti-angiogenesis agents such as angiostatin, anecortave acetate, thrombospondin, VEGF receptor tyrosine kinase inhibitors and anti-vascular endothelial growth factor (anti-VEGF) drugs such as ranibizumab and bevacizumab, pegaptanib, sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as acetbutolol, atenolol, bisoprolol, carvedilol, asmolol, labetalol, nadolol, penbutolol, pindolol, propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, pholpholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and/or unoprostone.

Other examples of drugs may also include, but are not limited to, anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluoroometholone, loteprednol, medrysone, fluocinolone acetonide, triamcinolone acetonide, triamcinolone, triamcinolone acetonide, beclomethasone, budesonide, flunisolide, fluorometholone, fluticasone, fludrocortisone, hydrocortisone, hydrocortisone acetate, loteprednol, rimexolone and non-steroidal anti-inflammatory agents including, for example, aspirin, diclofenac, flurbiprofen, ibuprofen, bromfenac, nepafenac, and ketorolac, salicylate, indomethacin, naxopren, piroxicam and nabumetone diflunisal, etodolac, fenoprofen, flurbiprofen, indomethacine, ketoprofen, meclofenamate, mefenamic acid, meloxicam, nabumetone, oxaprozin, piroxicam, salsalate, sulindac and tolmetin; COX-2 inhibitors like celecoxib, rofecoxib and Valdecoxib; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin, tobramycin, amikacin and streptomycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B, caspofungin, clotrimazole, fluconazole, itraconazole, ketoconazole, voriconazole, terbinafine, nystatin and miconazole; anti-malarial agents such as chloroquine, atovaquone, mefloquine, primaquine, quinidine and quinine; anti-mycobacterium agents such as ethambutol, isoniazid, pyrazinamide, rifampin and rifabutin; and/or antiparasitic agents such as albendazole, mebendazole, thiobendazole, metronidazole, pyrantel, atovaquone, iodoquinaol, ivermectin, paromycin, praziquantel, and trimatrexate.

Other examples of drugs may also include, but are not limited to, antiviral agents such as idoxuridine trifluorothymidine, acyclovir, cidofovir, famciclovir, gancyclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other antiviral agents such as interferons, ribavirin and trifluridiene; anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; and/or other anti-bacterials such as aztreonam, chloramphenicol, clindamycin, linezolid, nitrofurantoin and vancomycin.

Other examples of drugs may also include, but are not limited to, immune-modulating agents such as antiallergenics, including, for example, sodium chromoglycate, antazoline, methapyriline, chlorpheniramine, cetrizine, pyrilamine, prophenpyridamine; aldesleukin, adalimumab, azathioprine, basiliximab, daclizumab, etanercept, hydroxychloroquine, infliximab, leflunomide, methotrexate, mycophenolate mofetil, and sulfasalazine; anti-histamine agents such as azelastine, emedastine, loratadine, desloratadine, cetirizine, diphenhydramine, chlorpheniramine, dexchlorpheniramine, clemastine, cyproheptadine, fexofenadine, hydroxyzine, promethazine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor, transforming growth factor beta, somatotrapin, fibronectin, connective tissue growth factor, bone morphogenic proteins (BMPs), brain derived neurotrophic factor (BDNF), ciliary neurotrophic factor (CNTF), glial cell line-derived neurotrophic factor (GDNF), insulin-like growth factor (IGF), and nerve growth factor (NGF); and/or cytokines such as interleukins, CD44, cochlin, osteopontin, pleotrophin, midkine, vascular endothelial growth factor (VEGF), and serum amyloids, such as serum amyloid A.

Other therapeutic agents may include, but are not limited to, neuroprotective agents such as lubezole, nimodipine and related compounds, and including blood flow enhancers, sodium channels blockers, glutamate inhibitors such as memantine, neurotrophic factors, nitric oxide synthase inhibitors; free radical scavengers or anti-oxidants; chelating compounds; apoptosis-related protease inhibitors; compounds that reduce new protein synthesis; radiotherapeutic agents; photodynamic therapy agents; gene therapy agents; genetic modulators; and dry eye medications such as cyclosporine A, delmulcents, and sodium hyaluronate; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anticoagulant agents such as hirudin, aprotinin, argatroban, bivalirudin, desirudin, lepirudin, warfarin and ximelagatran; and/or anti-platelet agents such as abciximab, clopidogrel, dipyridamole, optifibatide, ticlopidine and tirofiban.

Other therapeutic agents may include, but are not limited to, prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-flurouracil (5-FU); immune modulating agents such as aldesleukin, imatinib, rituximab and tositumomab; mitotic inhibitors docetaxel, etoposide, vinblastine and vincristine; radioactive agents such as strontium-89; and/or other anti-neoplastic agents such as irinotecan, topotecan and mitotane.

Kits and Instructions

Also provided are kits containing any of the compositions described herein (e.g., a heterogeneous mixture of fetal neural retinal cells) suitable for use in any of the methods disclosed herein (e.g., treating a retinal disease or condition, or making or isolating a heterogeneous mixture of fetal neural retinal cell), including instructions for use thereof. Also provided are kits containing a composition, product of manufacture, or mixture or culture of cells (e.g., heterogeneous mixture of fetal neural retinal cells), wherein optionally the kit further includes instructions for practicing any of the methods described herein.

Kits may also include a cell population containing the mammalian retinal progenitor cells described herein, whether provided as cells in culture, fresh or frozen, or formulated as a composition for administration into a subject. Likewise, the kit may further include instructions for practicing any of the methods described herein. In some embodiments, such kits may additional contain an agent that binds one or more marker of retinal progenitor cells described herein (e.g., an antibody or oligonucleotide primer) and/or a basal or conditioned medium. In alternative embodiments, suitable kit may include: a first container containing an antibody specific for one or more markers, wherein said antibody is adapted for isolation or detection, e.g., by being conjugated to a fluorescent marker or magnetic bead; and a second container containing basal or conditioned medium. The kits may further include one or more additional reagents useful in the preparation of a cell population of the present invention, such as cell culture medium, extracellular matrix-coated cell culture dishes, and/or enzymes suitable for tissue processing. The kit may also include instructions regarding its use to isolate, purify, and/or expand the retinal progenitor cells or cell populations obtained from a tissue sample. Likewise, the kits may further contain a means for obtaining a tissue sample from a patient or donor, and/or a container to hold the tissue sample obtained.

Veterinary Applications

Any of the compositions and methods described herein can also be used for veterinary applications. For example, growing of feline RPCs, and the therapeutic application to the retina in a dystrophic cats and other animals, e.g. any mammalian pet, common domesticated and rare wild mammalian species, zoo animals, farm animals, sport (e.g., racing dogs or horses) animals, and the like.

There are a number of domesticated animals that harbor genes causing blindness as a result of extensive inbreeding. These included cats, dogs, and horses, and probably other species.

Likewise, there are retinal diseases and injuries that occur in wild and domestic animals that will benefit from treatment using the compositions and methods described herein.

Products of Manufacture, Implants and Artificial Organs

Also provided are implants and artificial organs, bioreactor systems, cell culture systems, plates, dishes, tubes, bottles and flasks and the like including one more of the compositions described herein containing a heterogeneous mixture of fetal neural retinal cells.

In alternative embodiments by way of non-limiting example, additionally provided herein are a bioreactor, implant, stent, artificial organ or similar devices containing a heterogeneous mixture of fetal neural retinal cells; for example, implants analogous to or as described in U.S. Pat. Nos. 7,388,042; 7,381,418; 7,379,765; 7,361,332; 7,351, 423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

EQUIVALENTS

The details of one or more embodiments of the invention are set forth in the accompanying description above. Although any methods and materials similar or equivalent to those described herein can be used in the practice or testing of the present invention, the preferred methods and materials are now described.

The foregoing description has been presented only for the purposes of illustration and is not intended to limit the invention to the precise form disclosed, but by the claims appended hereto.

A number of embodiments of the invention have been described. Nevertheless, it can be understood that various modifications may be made without departing from the spirit and scope of the invention. Accordingly, other embodiments are within the scope of the following claims.

What is claimed is:

1. A method of making a formulation comprising a heterogeneous mixture of non-immortal human fetal neural retinal cells, the method comprising:
   (a) mechanically and/or enzymatically dissociating an obtained sample of human retinal tissue cells from a human about 12 weeks to about 28 weeks gestational age to generate a dissociated suspension of cells and/or cell clusters,
   wherein the harvested sample of cells and/or small cellular clusters are enzymatically dissociated using trypsin or equivalent;
   (b) culturing the suspension in serum-free media in culture flasks or plates coated with a xeno-free fibronectin, an ornithine, a polylysine, or a laminin at standard oxygen levels for between about 4 and 6 passages, wherein the standard oxygen levels are about 20%;
   (c) freezing the suspension;
   (d) thawing the suspension; and
   (e) performing a second culturing step comprising culturing the thawed suspension in serum-free media at low oxygen levels for between about 3 and 6 passages such that the yield of cells obtained from said second culturing step at low oxygen levels is greater than the yield of cells obtained from an identical second culturing step performed at standard oxygen levels,
   wherein the low oxygen levels are between about 0.5% and about 10%,
   wherein the cells are passaged at between about 40% to 90% confluence and treated with an enzyme at each passage to dissociate the cells and the culture media is changed about every about 1 to 2 days.

2. The method of claim 1, wherein, following the subsequent culture culturing of the suspension at low oxygen levels, the cells are allowed to grow without passaging for a period of time at standard oxygen levels.

3. The method of claim 2, wherein, following the subsequent culture culturing of the suspension at low oxygen levels, the cells are allowed to grow without passaging for a period of time at standard oxygen levels for a period of time comprising between about 1 hour and 5 days.

4. The method of claim 1, wherein the low oxygen levels are selected from the group consisting of about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% oxygen.

5. The method of claim 1, wherein between about 0.01 mg/ml and 0.5 mg/ml vitamin C is included in the media changed every 1 or 2 days.

6. The method of claim 1, wherein the cells and/or cell clusters are cultured in a basal culture medium.

7. The method of claim 6, wherein the cells and/or cell clusters are cultured together with supplements or additives that support cell survival or growth.

8. The method of claim 7, wherein the cells and/or cell clusters are cultured together with supplements or additives that support cell survival or growth, and the supplements or additives that support cell survival or growth are selected from the group consisting of L-glutamine, human recombinant growth factors consisting of epidermal growth factor (EGF) and basic fibroblast growth factor (bFGF), and other growth factors.

9. The method of claim 1 wherein the media is supplemented with albumin, or recombinant albumin in an amount to have an initial concentration of about 1.0 mg/ml.

10. The method of claim 1, wherein:
    (a) the sample of cells is screened for the presence of a pathogen, a bacteria, an endotoxin, a fungus, a mycoplasma, a virus, a hepatitis virus or an HIV virus;
    (b) the sample of cells is screened for the presence of a normal karyotype;
    (c) the sample of cells does not exhibit elevated telomerase activity;
    (d) the sample of cells is screened for viability; or
    (e) the sample of cells is screened for tumorigenicity.

11. The method of claim 1, wherein the method for making the heterogeneous mixture of non-immortal human fetal neural retinal cells further comprises:
    (i) selecting human fetal neural retinal cells on the basis of cell surface or genetic markers, or
    (ii) selecting human fetal neural retinal cells on the basis of a human fetal neural retinal cell transcriptome profile, proteome profile or a genomic profile.

12. The method of claim 11, further comprising selecting the cells either before culturing or after culturing or both.

13. The method of claim 11, wherein the cell surface or genetic markers comprise CD15/Lewis X (LeX)/stage-specific embryonic antigen-1 (SSEAI) or GD2 ganglioside.

14. The method of claim 11, wherein the cell surface or genetic markers comprise CD9, CD81, CD133, Aquaporin 4 (AQP4) and/or C-X-C chemokine receptor type 4 (CXCR4).

* * * * *